(12) United States Patent
Jensen (10) Patent No.: US 8,040,127 B2
(45) Date of Patent: Oct. 18, 2011

(54) MULTI-SENSOR DISTORTION MAPPING METHOD AND SYSTEM

(75) Inventor: Vernon Thomas Jensen, Draper, UT (US)

(73) Assignee: General Electric Company, Schenectady, NY (US)

( * ) Notice: Subject to any disclaimer, the term of this patent is extended or adjusted under 35 U.S.C. 154(b) by 1397 days.

(21) Appl. No.: 11/504,436

(22) Filed: Aug. 15, 2006

(65) Prior Publication Data

US 2008/0079421 A1   Apr. 3, 2008

(51) Int. Cl.
*G01B 7/14* (2006.01)
*G01B 7/30* (2006.01)

(52) U.S. Cl. .............................. 324/207.16; 324/207.17

(58) Field of Classification Search ........... 324/207.15–207.17, 207.23, 207.26
See application file for complete search history.

(56) References Cited

U.S. PATENT DOCUMENTS

| | | | |
|---|---|---|---|
| 5,265,610 A | 11/1993 | Darrow et al. | |
| 5,443,006 A | 8/1995 | Beisel et al. | |
| 5,676,673 A | 10/1997 | Ferre et al. | |
| 5,829,444 A | 11/1998 | Ferre et al. | |
| 6,177,792 B1 * | 1/2001 | Govari et al. | 324/207.12 |
| 6,459,265 B1 | 10/2002 | Lou et al. | |
| 6,478,802 B2 | 11/2002 | Kienzle et al. | |
| 6,490,475 B1 | 12/2002 | Seeley et al. | |
| 6,493,573 B1 | 12/2002 | Martinelli et al. | |
| 6,553,326 B1 | 4/2003 | Kirsch et al. | |
| 6,666,579 B2 | 12/2003 | Jensen et al. | |
| 6,762,726 B2 * | 7/2004 | Alden et al. | 343/703 |
| 6,823,207 B1 | 11/2004 | Jensen et al. | |
| 7,640,121 B2 * | 12/2009 | Anderson | 702/66 |
| 2001/0036245 A1 | 11/2001 | Kienzle et al. | |
| 2004/0076259 A1 | 4/2004 | Jensen et al. | |
| 2004/0077940 A1 | 4/2004 | Kienzle et al. | |
| 2005/0228270 A1 | 10/2005 | Lloyd et al. | |
| 2006/0079756 A1 | 4/2006 | Lloyd et al. | |
| 2006/0115054 A1 | 6/2006 | Yatsenko et al. | |

* cited by examiner

*Primary Examiner* — Reena Aurora
(74) *Attorney, Agent, or Firm* — Fletcher Yoder, P.C.

(57) ABSTRACT

In one aspect of the present technique, an array of electromagnetic sensors is positioned within a volume of interest. In the presence of an electromagnetic field, the array of electromagnetic sensors is sampled to acquire signals representative of the location of the electromagnetic sensors in the array. The electromagnetic field distortion within the volume of interest is determined based on the acquired signals. In another aspect of the present technique, a system for detecting electromagnetic field distortions includes an electromagnetic sensor assembly for positioning within a volume of interest, a plurality of electromagnetic sensors for transmitting or receiving signals representative of the location of the electromagnetic sensors on the sensor assembly; and a tracker. In another aspect of the present technique, an electromagnetic sensor assembly for detecting electromagnetic field distortion includes a body, and an array of electromagnetic sensors positioned on the body.

13 Claims, 5 Drawing Sheets

MULTI-SENSOR DISTORTION MAPPING METHOD AND SYSTEM

BACKGROUND

The present invention relates generally to tracking systems that use magnetic fields such as for surgical interventions, and other medical procedures. More particularly, the present invention relates to apparatus and techniques for determining magnetic field distortion in such systems.

Tracking systems have been used to provide an operator (e.g., a physician) with information to assist in the precise and rapid positioning of a medical (e.g., surgical) device in a patient's body. In general, an image is displayed for the operator that includes a visualization of the patient's anatomy with an icon or image representing the device superimposed thereon. As the device is positioned with respect to the patient's body, the displayed image is updated to reflect the correct device coordinates. The image of the patient's anatomy may be generated either prior to or during the medical or surgical procedure. Moreover, any suitable medical imaging technique, such as X-ray, computed tomography (CT), magnetic resonance imaging (MRI), positron emission tomography (PET), and ultrasound, may be utilized to provide the basic image in which the device tracking is displayed.

To determine device location, tracking systems have utilized electromagnetic (EM) fields. During these procedures, signals are transmitted from one or more EM transmitters to one or more EM receivers. In one example, an EM receiver is mounted in an operative end of the device. In general, the EM transmitters generate an electromagnetic field that is detected by the EM receivers and then processed to determine the device location, for example, the position and orientation, including the X, Y and Z coordinates and the roll, pitch and yaw angles.

However, as those of ordinary skill in the art appreciate, the presence of field distorting objects may result in distortions in the magnetic field emitted from the EM transmitters and thereby change the magnitude and direction of this field. For example, the presence of a signal from another source, the magnetic field of the eddy current in a conductive object, or the field distorting effect of a ferro-magnetic object can result in these distortions. Unless compensated for, these distortions will result in error in the determined location of the device. One source of magnetic field distortions may be the equipment utilized in the tracking system itself. For example, certain tracking systems include a fixture containing one or more EM sensors that are attached to an imaging system, such to the C-arm of an X-ray fluoroscopy system. As those of ordinary skill in the art will appreciate, these imaging systems typically include conducting objects (e.g., the C-arm) that result in the above-described field distortions. To compensate for this known distortion, a distortion map is generally created for each tracking system during the factory calibration process. This distortion map is used by the tracking system to compensate for this known distorting effect during the medical procedure.

An exemplary technique for creating the distortion map for a tracking system that includes an X-ray fluoroscopy system containing a C-arm, involves use of a precision robot. An EM transmitter is attached to an arm of the robot and moved to numerous points in space within the navigated volume. At each point, signals from the EM transmitter are detected by one or more EM receivers and then processed to determine a measured location of the transmitter with respect to the receiver, which is rigidly fixed to the C-arm of the X-ray fluoroscopy system. Because a precision robot is used, the real world location of the transmitter at each sampled point in the navigated volume is known. Accordingly, the measured location of the device detected by the receivers is compared to the transmitter's real world location to generate the distortion map that is used by the tracking system. By way of example, the distortion map may cross-reference the measured transmitter location with the real world transmitter location. However, to generate a complete distortion map, the transmitter must be positioned at thousands of points within the navigated volume. This process of collecting thousands of data points is time consuming and resource intensive. Moreover, extra time may be required to allow for the robot arm to stabilize at each point, and extreme care must be used to ensure that the system is not disturbed during data acquisition.

In addition to the tracking system itself, field distorting objects also may be present in the clinical environment where the tracking system is used. However, the impact of these field distorting objects on the magnetic field in the clinical environment is generally not known, and the field distorting objects are frequently transient. Techniques for detecting distorting objects during medical procedures have been developed. One such technique utilizes two sensors rigidly mounted at a known fixed distance on the medical device to detect uniform distortions in the area of the medical device. However, these techniques only detect field distortions in the immediate vicinity of the two sensors and do not convey the extent of field distortions in the larger navigated volume.

Accordingly, there is a need for an improved technique for detecting and correcting for magnetic field distortions. Particularly, there is a need for a technique that detects magnetic field distortions in and around a tracking system so that these distortions can be accounted for in the clinical environment.

BRIEF DESCRIPTION

The present technique provides a novel method and apparatus for determining electromagnetic field distortions. In accordance with one embodiment of the present technique, a method is provided for determining electromagnetic field distortion. The method includes positioning an array of electromagnetic sensors in a volume of interest. The method further includes sampling the array of electromagnetic sensors, in the presence of an electromagnetic field, to acquire signals representative of the location of the electromagnetic sensors in the array. The method also includes determining an electromagnetic field distortion within the volume of interested based on the acquired signals.

In accordance with another aspect of the present technique, a system for detecting electromagnetic field distortions is provided. The system includes an electromagnetic sensor assembly for positioning within a volume of interest. The electromagnetic sensor assembly includes a body, and an array of electromagnetic sensors positioned on one or more surfaces of the body. The system further includes a plurality of electromagnetic sensors for transmitting or receiving signals representative of the location of the electromagnetic sensors in the array. The system also includes tracker configured to acquire the signals representative of the location of the electromagnetic sensors in the array, and determine electromagnetic field distortion within the volume of interest based on the signals.

In accordance with yet another aspect of the present technique, an electromagnetic sensor assembly for detecting electromagnetic field distortion is provided. The electromagnetic sensor assembly includes a body, and an array of electromagnetic sensors positioned on one or more surfaces of the body.

The array of electromagnetic sensors may be positioned on the body in a linear array, a two-dimensional array, or a three-dimensional array.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
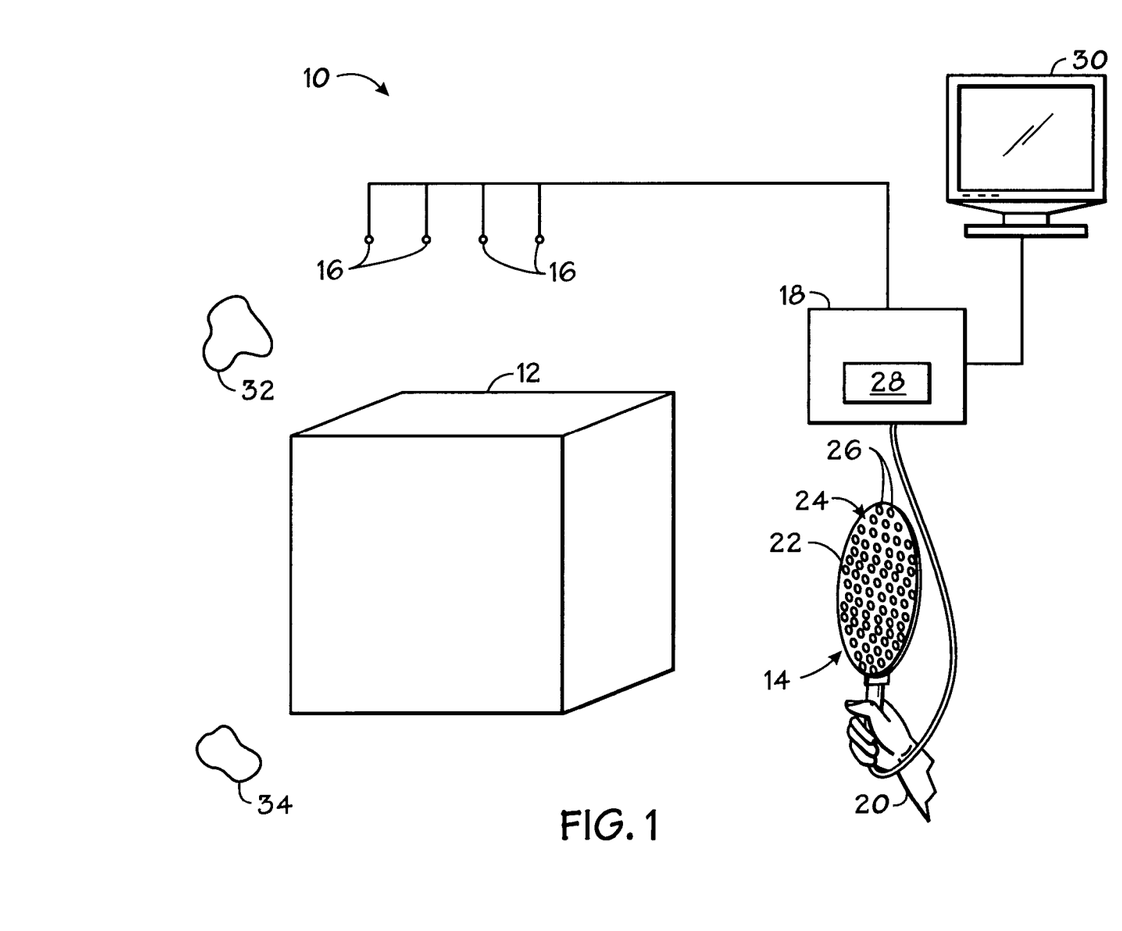
FIG. 1 is a schematic illustration of an exemplary system for detecting magnetic field distortions implementing certain aspects of the present technique.

FIG. 1 illustrates diagrammatically a system 10 for detecting field distortions within a volume of interest 12. As illustrated, the system 10 generally includes an EM sensor assembly 14, a plurality of EM sensors 16, and a tracker 18.

In the illustrated embodiment, an operator (represented in FIG. 1 by hand 20) employs the EM sensor assembly 14 to detect field distortions within the volume of interest 12. The volume of interest 12 may be any suitable volume where it is desired to determine magnetic field distortions. For example, the volume of interest 12 may be a volume to be navigated by a medical device, wherein a tracking system will be used to determine the location of the medical device in the volume of interest 12. EM sensor assembly 14 comprises a body 22 and an array 24 of EM sensors 26 positioned on a surface of the body 22. In general, the operator 20 moves the EM sensor assembly 14 through the volume of interest 12 so that signals are transmitted from one or more sample locations within the volume of interest. At each sample location, a signal should be transmitted from each EM sensor 26 in the array 24. Alternatively, in certain embodiments, the array 24 of EM sensors 26 may serve as receivers so that signals are received at one or more sample locations within the volume of interest 12.

By way of example, the array 24 of EM sensors 26 may be implemented as field generators with each sensor 26 including three orthogonally disposed magnetic dipoles (e.g., current loops or electromagnets). Electromagnetic fields generated by each of the dipoles are distinguishable from one another by phase, frequency, time division multiplexing, and the like. As those of ordinary skill in the art will appreciate, the near-field characteristics of the electromagnetic fields may be used for coordinate determination. Other suitable techniques for using the array 24 of EM sensors 26 for generating a field in which location detection may be achieved within the volume of interest 12 may utilized with the present technique.

The system 10 further includes a plurality of EM sensors 16 for receiving signals from the array 24 of EM sensors 26. The plurality of EM sensors 16 output these signals to the tracker 18 for processing. The tracker 18 processes these signals to determine a measured location for each sensor 26 of the array 24 at each sample location within the volume of interest 12. The measured location may typically include the position (the X, Y and Z coordinates), as well as the orientation (roll, pitch, and yaw angles). Alternatively, in certain embodiments, the plurality of EM sensors 16 may serve as transmitters that transmit signals to the array 24 of EM sensors 26.

The tracker 18 typically includes memory 28. It should be noted that any type of memory may be utilized in tracker. For example, memory 28 may be any suitable processor-readable media that is accessible by the tracker 18. Moreover, the memory 28 may be either volatile or non-volatile memory.

A display 30 coupled to the tracker 18 may be utilized to control the acquisition of data from within the volume of interest 12. By way of example, the display 30 may be used to provide graphic feedback indicating areas within the volume of interest 12 that need additional data.

As those of ordinary skill in the art will appreciate, the presence of field distorting objects 32, 34 in or near the volume of interest 12 will result in distortions in the EM field generated by the array 24 of sensors 26. For example, the field distorting objects 32, 34 may be tables, fixtures, tools, electronic equipment, one or more components of an imaging system (e.g., a C-arm). One or more of these objects may be present in a clinical environment that would then distort EM fields used, for example, in EM device tracking.

As those of ordinary skill in the art will appreciate, the presence of the field distorting objects 32, 34 may generally result in errors in the measured location for the array 24 of sensors 26 determined by the tracker 18. However, the actual mechanical location of each of the sensors 26 with respect to the other sensors 26 in the array 24 is known. Based on this known mechanical location, the field distortion of the measured location for each of the sensors 26 in the array 24 within the volume of interest 12 can be determined. As such, the present technique allows for the detecting and reporting these field distortions caused by stationary and/or moving objects in, and around, the volume of interest 12. In some embodiments, based on the field distortion, the compatibility of the volume of interest 12 for use with EM device tracking could be determined. Alternatively, the determined field distortions at the one or more sample locations may also be used to calibrate the tracker 18. For example, a look-up table may be created that, for example, cross-references the undistorted sensor locations with the distorted sensor locations.

Figure 2:
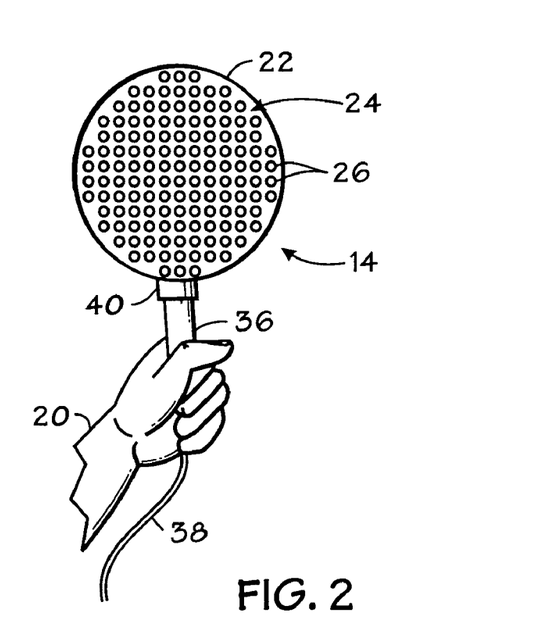
FIG. 2 is a schematic representation of an exemplary sensor assembly in accordance with certain aspects of the present technique.

Referring now to FIG. 2, a sensor assembly 14 in accordance with one embodiment of the present technique is illustrated. In the illustrated embodiment, EM sensor assembly 14 comprises a body 22 and an array 24 of EM sensors 26 positioned on one or more surfaces of the body 22. In general, body 22 may be rigid so that the distance between the sensors 26 in the array 24 is fixed. Alternatively, the array 24 of EM sensors 26 may be mounted on body 22 using any suitable technique. For example, to maintain the fixed distance a rigid mount may be used to fix the EM sensors 26 to body 22. While the body 22 is illustrated as having a generally circular shape, those or ordinary skill in the art will appreciate the body 22 may have any suitable shape for positioning the two-dimensional array of sensors. For example, one side of body 22 may have a generally rectangular shape or elliptical shape. As illustrated, the sensors 26 in the array 24 are positioned on the surface of the body 22 in a two-dimensional array. The distance between the sensors 26 in the array 24 is thus fixed and known. However, those of ordinary skill in the art will appreciate that the sensors may be suitably spaced so as not to undesirably affect the sensing accuracy of a particular sensor with respect to its neighbors based on a variety of factors, including sensor size, range, and sensitivity. It should be noted that, while FIG. 2 illustrates uniform spacing between the sensors 26 in the array 24, a sensor assembly 14 comprising an array 24 of sensors 26 with non-uniform spacing is also encompassed by the present technique.

Sensor assembly 14 further comprises handle assembly 36 connected to sensor assembly 14 to enable handling of sensor assembly 14. In addition, cable 38 connected to sensor assembly 14 provides the necessary lead and/or wires for connection with EM sensors 26 for proper operation of sensor assembly 14. Moreover, sensor assembly 14 may comprise a variety of additional electronics, such as a multiplexer 40. In the illustrated embodiment, multiplexer 40 is located between the body 22 and the handle assembly 36.

Figure 3:
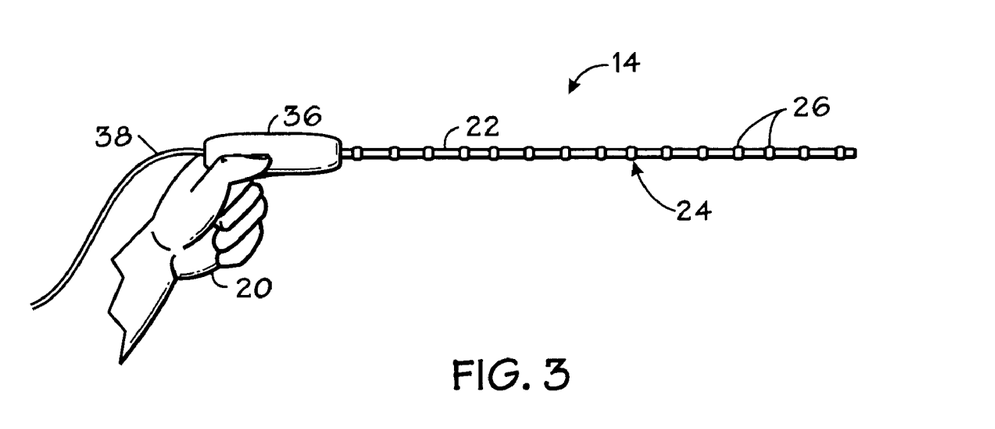
FIG. 3 is a schematic representation of an alternative sensor assembly.

FIG. 3 illustrates a variation of sensor assembly 14 suitable for use with the present technique. In this variation, the EM sensors 26 in the array 24 are positioned on body 22 in a linear array. While body 22 may have any suitable shape for positioning the linear array of sensors, in the example of FIG. 3, body 22 has a generally rod-like shape. Handle assembly 36 is connected to sensor assembly 14 to enable handling of sensor assembly 14. Cable 38, connected to sensor assembly 14, provides the necessary lead and/or wires for connection with EM sensors 26 for proper operation of sensor assembly 14.

Figure 4:
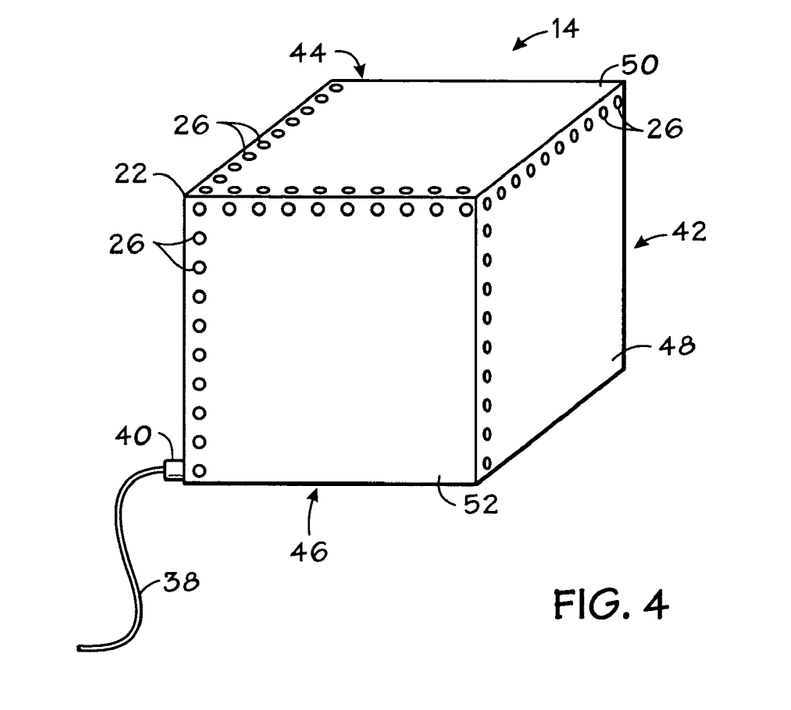
FIG. 4 is a schematic representation of another alternative sensor assembly.

FIG. 4 illustrates another variation of sensor assembly 14 suitable for use with the present technique. Sensor assembly 14 includes a three-dimensional array of EM sensors 26. The three-dimensional array of EM sensors 26 includes a plurality of two-dimensional transmitter arrays on different planes, including first two dimensional array 42, second two dimensional array 44, and third two dimensional array 46. For simplicity, only a portion of the sensors in each of the two-dimensional arrays is illustrated on FIG. 4. As illustrated, the plurality of two-dimensional arrays 42, 44, 46 of EM sensors 26 are positioned on a plurality of sides of the illustrated device. As illustrated, first two dimensional array 42, second two dimensional array 44, and third two dimensional array 46 are respectively located on first side 48, second side 50, and third side 52 of the body 22. As will be appreciated, two-dimensional sensor arrays may be positioned on one or more of the remaining sides of body 22. While body 22 is illustrated as a cube having four different sides, those of ordinary skill in the art will appreciate that body may be any suitable shape configured to allow placement of a plurality of two-dimensional transmitter arrays in two or more planes. Cable 38 connected to sensor assembly 14 provides the necessary lead and/or wires for connection with EM sensors 26 for proper operation of sensor assembly 14. Moreover, as illustrated on FIG. 4, sensor assembly 14 further comprises multiplexer 40 coupled to body 22.

In one embodiment of the present technique, the system 10 of FIG. 1 is used to detect field distortions within the volume of interest 12. For example, referring to FIG. 5, exemplary acts for detecting field distortion and using the system 10 of FIG. 1 are depicted. Generally, to detect field distortions, the EM sensor assembly 14 is positioned (Block 48) within the volume of interest 12. As previously mentioned, the EM sensor assembly 14 contains an array 14 of EM sensors 26. In the presence of an electromagnetic field, the array 14 of EM sensors 26 may then be sampled (Block 50) at a sample location within the volume of interest 12 as the sensor assembly 14 is positioned. By sampling the array 24 of EM sensors 26, signals representative of the location of each of the EM sensors 26 in the array 24 are acquired. For example, in instances where the EM sensors 26 are transmitters, the signals are transmitted from the EM sensors 26 to a plurality of EM receivers (for example, the plurality of EM sensors 16). Alternatively, in instances where the EM sensors 26 are receivers, the signals are received by the EM sensors 26 from a plurality of EM transmitters (for example, the plurality of EM sensors 16).

Figure 6:
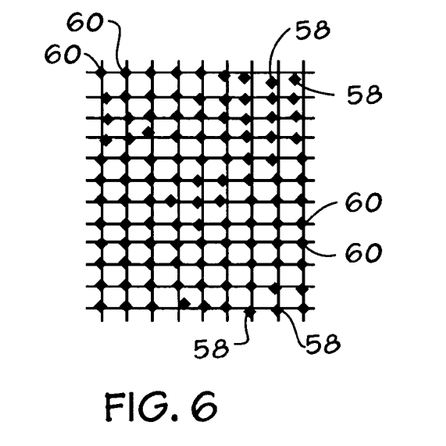
FIG. 6 is a graphical representation illustrating measured sensor locations of a sensor assembly at one point in a volume of interest.

The signals may then be suitably processed to determine the measured sensor location (Block 52) for each of the EM sensors 26 in the array 24. By way of example, the measured location may include the sensor position and orientation. FIG. 6 illustrates the measured sensor location for each of the EM sensors 26 in the array 24 on a two-dimensional grid. As illustrated by FIG. 6, due to the presence of the field distorting objects 32, 34 (depicted on FIG. 1), the measured sensors locations for one or more of the EM sensors 26 in the array 24 may be distorted. Accordingly, the distorted sensor locations are represented by reference numeral 58, and the undistorted sensor locations are represented by reference numeral 60.

Figure 7:
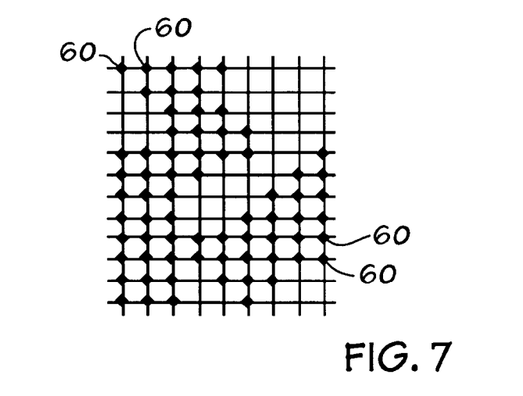
FIG. 7 is a graphical representation illustrating the measured sensor locations of FIG. 6 after the distorted measurements have been filtered.

Referring again to FIG. 5, established sensor locations for each EM sensor 26 in the array 24 are then determined (Block 54). In general, the established sensor locations correspond to the "true" or "real world" sensor locations for the EM sensors 26 in the volume of interest when sampled. The established sensor locations for a portion of the EM sensors 26 in the array can be determined by determining which of the measured sensor locations are undistorted. As will be appreciated, the undistorted sensor locations 60 should generally correspond to the established sensor locations for this portion of the EM sensors 24. By way of example, to determine the undistorted sensor locations 60, the measured sensor locations for the EM sensors 26 in the array 24 may be compared to the known geometry of the array 24. In accordance with certain implementations of the present technique, if the distance between the measured sensor location for a particular EM sensor and the known geometry is greater than a preset or known value, the measured sensor location may be considered distorted. Other suitable techniques for determining which of the measured sensor locations are distorted are also encompassed within the present technique. Accordingly, based on this comparison, the measured sensor location of each of the EM sensors 26 in the array 24 may be evaluated to determine whether the measured sensor location for that particular EM sensor is distorted. Thereafter, the distorted sensor locations 58 may be filtered so that only the undistorted sensor locations 60 remain. Accordingly, the "true" or "real world" sensor locations for a portion of the EM sensors 26 has now been established, in that these undistorted sensor locations 60 generally correspond to established sensor locations. FIG. 7 illustrates a two dimensional grid containing only the undistorted sensor locations 60 after the distorted sensor locations 58 have been filtered. As illustrated by FIG. 7, after the distorted sensor locations have been filtered, the true location for the remaining EM sensors 26 in the array 24 are unknown. Therefore, the true location for the remaining EM sensors 26 should be determined.

The true location for the remaining EM sensors 26 in the array 24 may be established based on the established sensor locations that correspond to the undistorted sensor locations 60. As mentioned above, the geometry of the array 24 of EM sensors 26 is known a priori. Likewise, the established sensor locations corresponding to the undistorted sensor locations 60 are also known. Accordingly, the known geometry of the array 24 of EM sensors 26 may be compared to these established sensor locations. In one embodiment, this comparison involves aligning the known geometry of the array 24 with the established sensor locations corresponding to the undistorted sensor locations 60.

Figure 8:
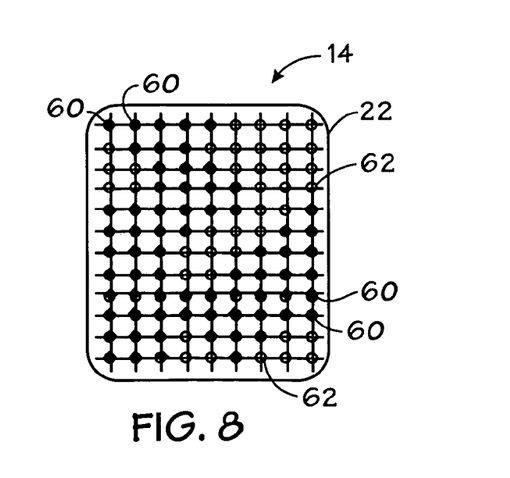
FIG. 8 is a graphical representation illustrating the established sensor locations of a sensor assembly based on the measured sensor locations of FIG. 7.

By way of example, FIG. 8 illustrates a two-dimensional grid containing the established sensor locations for each of the EM sensors 26 in the array 24. In the illustrated embodiment, sensor assembly 14 containing the array 24 of EM sensors is aligned with the established sensor locations corresponding to the undistorted sensor locations 60. The true location of the remaining EM sensors 26 may then be established, in that the established sensor location for the remaining EM sensors generally corresponds to the location of the corresponding EM sensor in the array 24. The established sensor location for the remaining EM sensor is generally represented on FIG. 8 by reference numeral 62.

Figure 5:
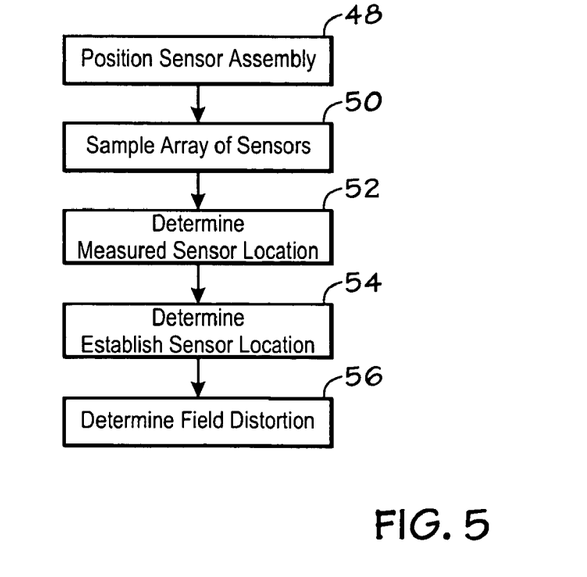
FIG. 5 is a block diagram of an exemplary technique for detecting magnetic field distortions.

The field distortion may then be determined (block 56) based on this comparison. For example, to determine field distortion at the sample location, the established sensor locations 62 for the remaining EM sensors are then compared (block 62) to the distorted sensor locations 58. To determine the field distortion at multiple sample locations within the volume of interest 12, the acts contained in steps 48-56 may be repeated at each sample location. For example, the array 24 of sensors 26 may be repeatedly sampled as sensor assembly 14 is continuously moved through the volume of interest 12. In certain embodiments, the sensor assembly 14 may be attached to a robot arm that moves sensor assembly 14 through the volume of interest 12. Alternatively, the sensor assembly 14 may have a sufficient number of sensors 26 so that a sufficient amount of distortion data is acquired at a single sample location within the volume of interest 12.

As those of ordinary skill in the art will appreciate, the field distortion determined in accordance with the present technique may allow for the field distortions to be accounted for in a clinical environment. By way of example, if the field distortion exceeds a preset value, the system 10 may report a field integrity violation. A field integrity violation may be reported if the field distortion at one or more sensor locations within the volume of interest exceeds a preset value. The reported field integrity violation may include a message on display 30, or it may be in the form of an audible alarm. To determine whether the field distortion is undesirable for the particular EM application, a number of different techniques may be used. In certain embodiments, the distance between the established and the measured sensor location for each EM sensor may be monitored, for example, as the array 24 of EM sensors is sampled at one or more sample locations within the volume of interest 12. If this monitored distance exceeds a preset value between the established and the measured sensor location, a field integrity violation may be reported. In certain embodiments, the difference between measured location and the established location for each of the X, Y and Z coordinates and the roll, pitch and yaw angles may be monitored, for example, as the array 24 of EM sensors 26 is sampled at one or more sample locations within the volume of interest 12. If the difference for any one of the measurements exceeds a preset value, a field integrity violation may be reported. In certain embodiments, a weighted sum of the coordinates for all six measurements (the X, Y and Z coordinates and the roll, pitch and yaw angles) may be monitored. If the difference between the weighted sum for the measured coordinates and the established coordinates, exceeds a preset value, a field integrity violation may be reported.

Once a field integrity violation is reported, the electromagnetic compatibility or mapping of the volume of interest may be known. In certain embodiments, the field distortion may potentially be corrected. For example, the environment surrounding the volume of interest 12 may be examined and one or more field distorting objects may be moved away from the volume of interest 12 to reduce, or even eliminate, the field distortion. For example, a table or tool not needed for subsequent operations may be removed from the clinical environment. Thereafter, the example acts 48-56 may be repeated to determine if the field distortion has been corrected.

In addition, the field distortion determined in accordance with the present technique also could be used to calibrate the tracker 18. This calibration may be done in a clinical or a factory environment. By way of example, this known field distortion may be used, for example, to calibrate the tracker 18 to automatically correct measured sensor locations to account for the presence of the distorting objects 32, 34. This calibration may be useful during factory calibration, so that known distorting objects, such as a C-arm or other equipment associated with a tracking system, can be accounted for by tracker 18 prior to field use. In certain embodiments, the calibration may include inputting a distortion map into the tracker 16. For example, to calibrate the tracker 18, a look-up table may be created that, for example, cross-references the measured sensor location with the established sensor location for each of the sensors 26 in the array 24 at multiple positions of the transmitter assembly 14 within the volume of interest 12.

Figure 9:
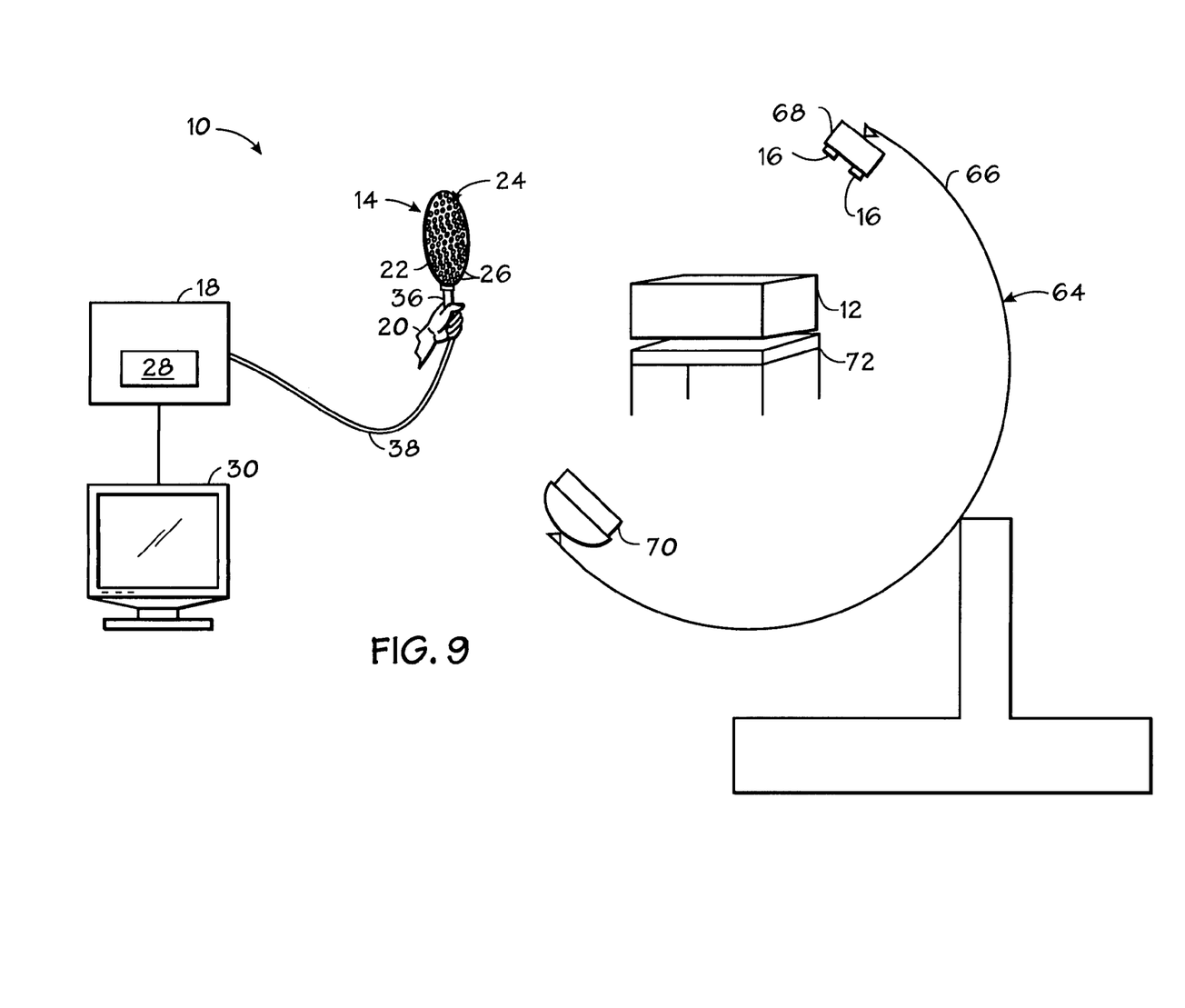
FIG. 9 is a schematic illustrating a fluoroscopy imaging system and the system of FIG. 1 for calibrating the fluoroscopy imaging system, in accordance with one embodiment of the present technique.

As previously mentioned, the present technique may be used in the calibration of tracker 18 to determine field distortions caused by an X-ray fluoroscopy system. Referring now to FIG. 9, X-ray fluoroscopy system 64 is illustrated. In addition, FIG. 9 illustrates system 10 including the EM sensor assembly 14, the plurality of sensors 16, tracker 18, and display 30.

In general, the X-ray fluoroscopy system 64 includes a C-arm 66, an X-ray radiation source 68, and X-ray detector 70. The X-ray radiation source 68 is mounted on the C-arm 66, and the X-ray detector 70 is mounted on the C-arm 66 in an opposing location from the X-ray radiation source 68. While in some systems the X-ray radiation source 68 and the X-ray detector 70 are fixed, in a typically fluoroscopy system the C-arm 66 allows for movement of the X-ray radiation source 68 and the X-ray detector 70 about the volume of interest 12. In operation, the X-ray radiation source 68 emits a stream of radiation suitable for X-ray fluoroscopy. The X-ray detector 70 receives a portion the stream of radiation from the X-ray source 68 that passes through the volume of interest 12 in which a subject (not shown), such as a human patient, is positioned on table 72. The X-ray detector 70 produces electrical signals that represent the intensity of the radiation stream. As those of ordinary skill in the art will appreciate, these signals are suitably acquired and processed to reconstruct an image of features within the subject.

In the illustrated embodiment, an operator 20 (represented on FIG. 9 by a hand) employs the EM sensor assembly 14 to detect field distortions within the volume of interest 12. As previously mentioned, the EM sensor assembly 14 comprises a body 22 and an array 24 of EM sensors 26 positioned on a surface of the body 22. Signals are acquired from sampling the array 24 at one or more sample locations within the volume of interest 12. The system 10 further includes a plurality of EM sensors 16 that, in one embodiment, receive signals from the array 24 of EM sensors 26. In general, the plurality of EM sensors 16 may be fixed relative to the C-arm 66. In the illustrated embodiment, the plurality of EM sensors 16 is fixed on the X-ray radiation source 68, which is mounted on the C-arm 66. In some embodiment, the plurality of EM sensors 16 may be mounted on a calibration fixture (not shown), which is fixed to the C-arm. The acquired signals are output to the tracker 18 suitably for processing. The tracker 18 processes these signal to determine the measured location for each of the EM sensors 26 in the array 24.

As those of ordinary skill in the art will appreciate, the components of the X-ray fluoroscope 64, including the C-arm 66 and the table 72, will typically result in distortions in the field generated by the system 10. Due to this field distortion, errors in the measured sensor locations may result. The field distortion then may be used to calibrate the tracker 18 to account for field distorting effect of the X-ray fluoroscopy system 64. For example, as previously mentioned, a look-up table may be created that, for example, cross-references the measured sensor locations with the established sensor locations for each of the EM sensors 26 in the array 24 at multiple positions of the EM sensor assembly 14 within the volume of interest 12.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for determining electromagnetic field distortion, comprising:
   positioning an array of electromagnetic sensors in a volume of interest;
   sampling the array of electromagnetic sensors, in the presence of an electromagnetic field, to acquire signals representative of locations of the electromagnetic sensors; and
   determining distortion of the electromagnetic field within the volume of interest based on the acquired signals.

2. The method of claim 1, comprising determining a measured location for each of the electromagnetic sensors in the array based on the acquired signals.

3. The method of claim 2, comprising evaluating the measured locations of the electromagnetic sensors to determine established locations of a portion of the electromagnetic sensors.

4. The method of claim 3, comprising determining established locations of the remaining electromagnetic sensors based on the established locations of the portion of the electromagnetic sensors.

5. The method of claim 4, comprising comparing the measured locations of the remaining sensors to the established locations of the remaining sensors.

6. The method of claim 5, wherein determining distortion of the electromagnetic field is based on the comparison of the measured locations of the remaining sensors to the established locations of the remaining sensors.

7. The method of claim 1, wherein the array of electromagnetic sensors is repeatedly sampled as the array is continuously moved through the volume of interest.

8. The method of claim 1, comprising moving one or more field distorting objects away from the volume of interest based on the determined distortion of the electromagnetic field.

9. The method of claim 1, comprising creating a distortion map of the volume of interest based on the determined distortion of the electromagnetic field.

10. The method of claim 1, comprising calibrating a tracking system based on the determined distortion of the electromagnetic field so the tracking system can account for the determined distortion of the electromagnetic field.

11. A system for detecting electromagnetic field distortions, comprising:
    an electromagnetic sensor assembly for positioning within a volume of interest, the electromagnetic sensor assembly comprising a body, and an array of electromagnetic sensors positioned on one or more surfaces of the body;
    a plurality of electromagnetic sensors for transmitting or receiving signals representative of the location of the electromagnetic sensors in the array; and
    a tracker configured to acquire the signals representative of the location of the electromagnetic sensors in the array, and to determine distortion of an electromagnetic field within the volume of interest based on the signals.

12. The system of claim 11, wherein the electromagnetic sensors in the array are configured to transmit electromagnetic signals.

13. The system of claim 11, wherein the plurality of electromagnetic sensors are fixed in relation to an X-ray fluoroscopy system.

* * * * *